United States Patent [19]

Gyure et al.

[11] Patent Number: 5,669,889

[45] Date of Patent: Sep. 23, 1997

[54] NEEDLE SHIELD ASSEMBLY HAVING A SINGLE-USE LOCK

[75] Inventors: Sandor Gyure, West Orange; Niall Sweeney, Rutherford; Albert Newman, West Orange, all of N.J.

[73] Assignee: Becton, Dickinson and Company, Franklin Lakes, N.J.

[21] Appl. No.: 675,753

[22] Filed: Jul. 3, 1996

[51] Int. Cl.⁶ .................................................. A61M 5/32
[52] U.S. Cl. ........................... 604/263; 604/192; 128/919
[58] Field of Search ................................. 604/192, 187, 604/263, 11; 128/919

[56] References Cited

U.S. PATENT DOCUMENTS

| | | | |
|---|---|---|---|
| 3,658,061 | 4/1972 | Hall | 128/214.4 |
| 4,664,259 | 5/1987 | Landis | 604/263 X |
| 4,872,552 | 10/1989 | Unger | 206/365 |
| 4,886,503 | 12/1989 | Miller | 604/192 |
| 4,909,792 | 3/1990 | Norelli | 604/192 |
| 5,055,102 | 10/1991 | Sitnik | 604/192 |
| 5,116,325 | 5/1992 | Paterson | 604/192 |
| 5,135,509 | 8/1992 | Olliffe | 604/192 |
| 5,188,611 | 2/1993 | Orgain | 604/192 |
| 5,242,417 | 9/1993 | Paudler | 604/192 |
| 5,374,255 | 12/1994 | Nathan et al. | 604/192 |
| 5,445,619 | 8/1995 | Burns | 604/192 |
| 5,462,534 | 10/1995 | Debreczeni | 604/192 |
| 5,486,163 | 1/1996 | Haynes | 604/192 |
| 5,490,841 | 2/1996 | Landis | 604/110 |
| 5,509,907 | 4/1996 | Bevilacqua | 604/263 |

Primary Examiner—John D. Yasko
Attorney, Agent, or Firm—John L. Voellmicke

[57] ABSTRACT

A needle shield assembly having a single-use lock includes a needle cannula having a proximal end connected to a hub. A collar is connected to the hub and an elongate rigid needle cover removably engages the hub and covers the needle cannula. An elongate needle shield is hingedly connected to the collar. The needle shield has two side walls defining a longitudinal opening. The needle shield is capable of pivoting from an open position where the needle cannula is exposed, to a closed needle protecting position where the needle cannula is within the longitudinal opening of the needle shield. Structure is provided for preventing the needle shield from being pivoted into the closed needle protecting position until the needle cover is removed. Structure is also provided for automatically locking the needle shield in the closed needle protecting position when the needle shield is pivoted into the closed position.

20 Claims, 5 Drawing Sheets

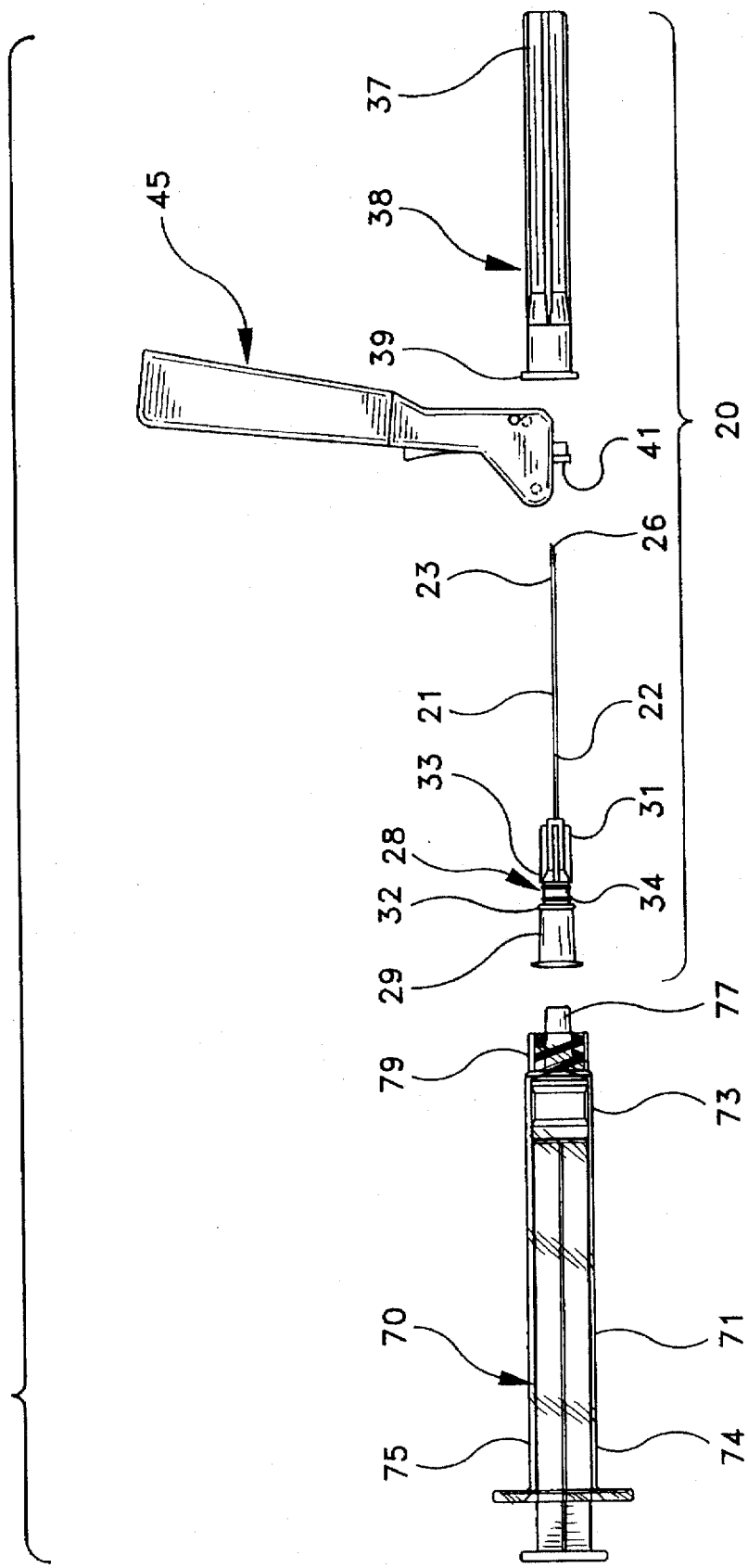

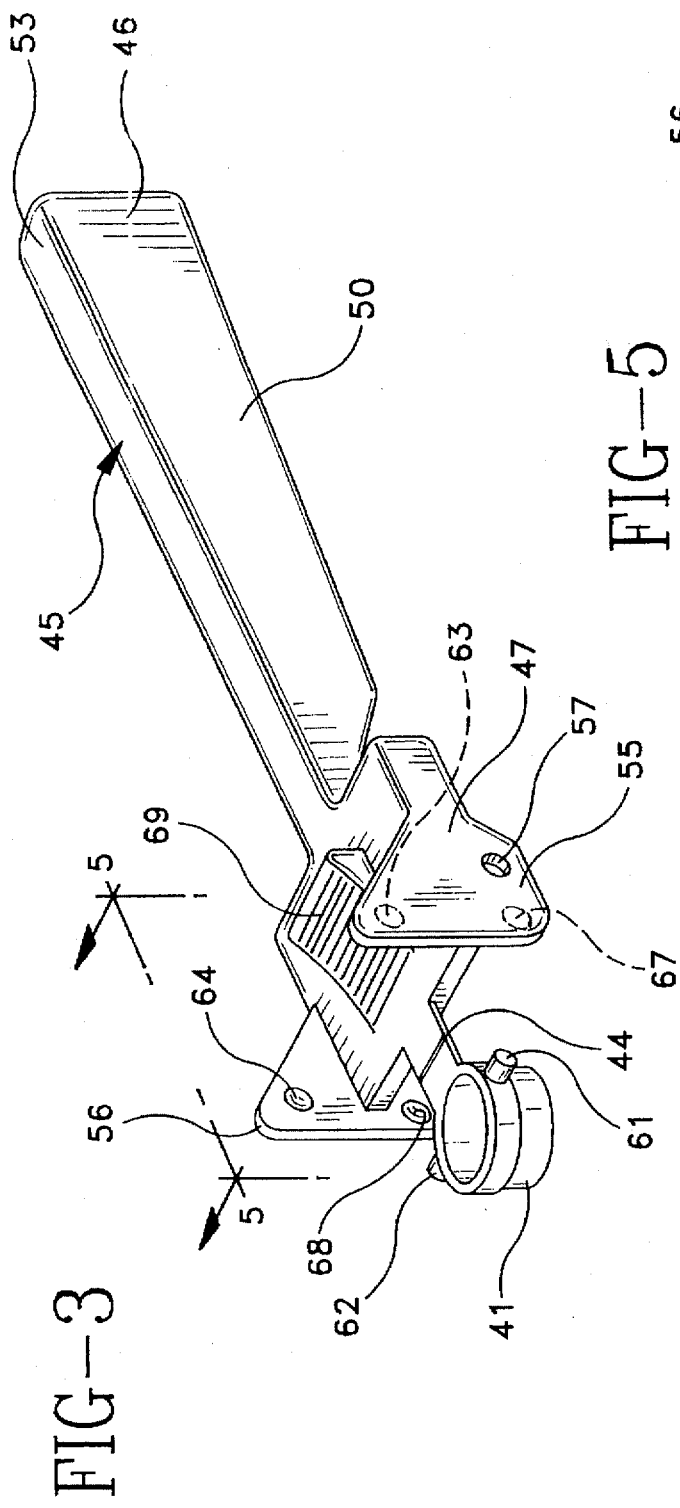
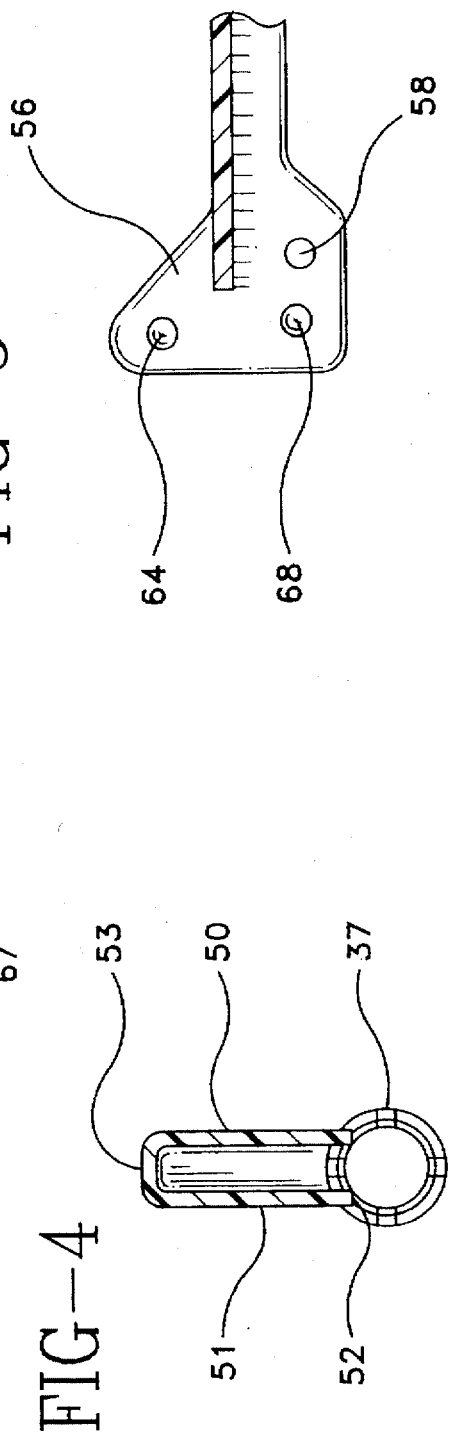

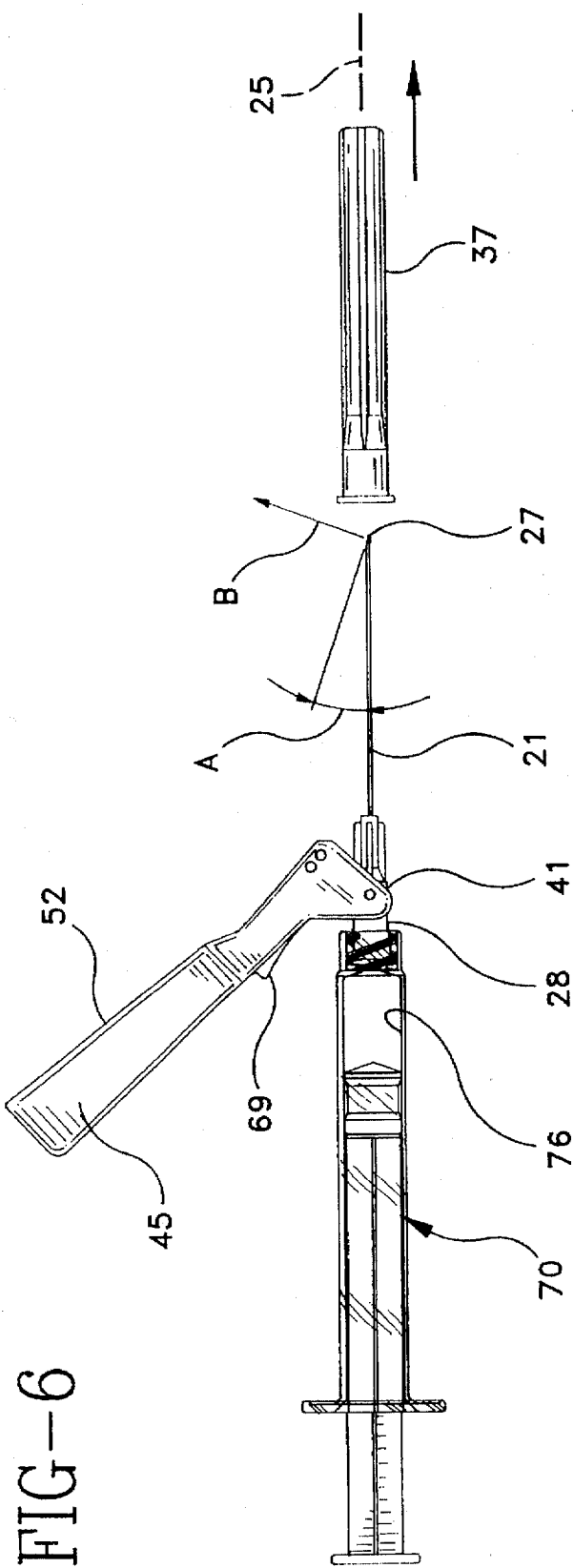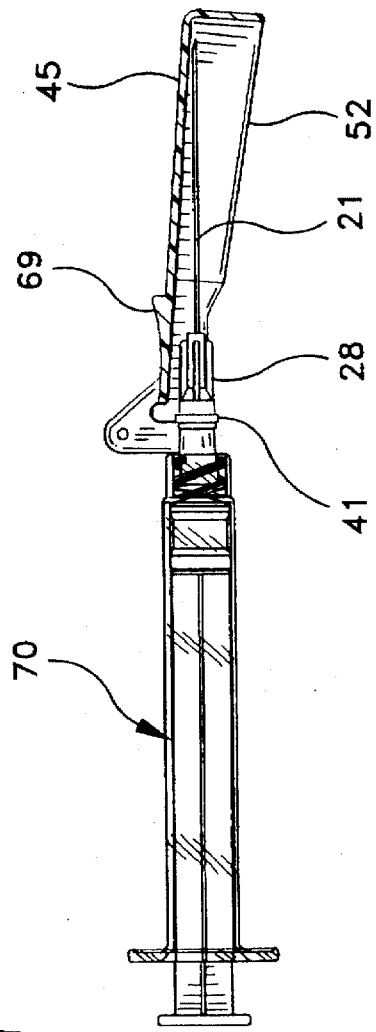
FIG-6
FIG-7

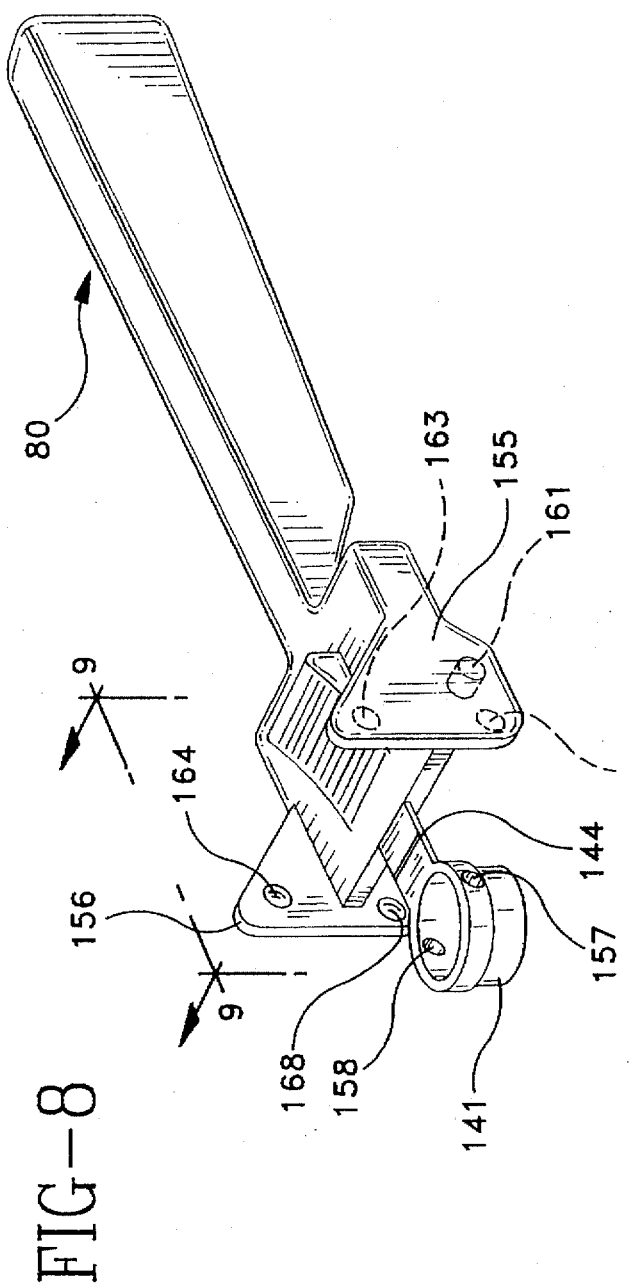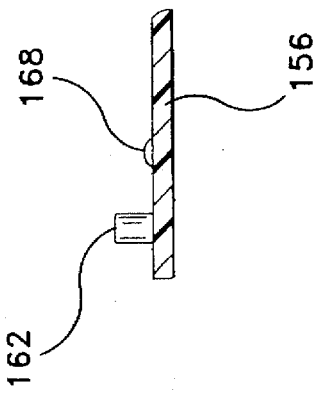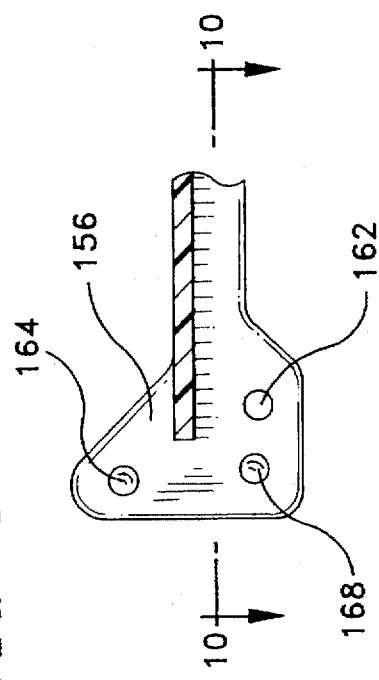

NEEDLE SHIELD ASSEMBLY HAVING A SINGLE-USE LOCK

FIELD OF THE INVENTION

The subject invention relates to needle shields for hypodermic needles, catheter needles and other medical implements to help prevent accidental contact with the needle.

BACKGROUND

Accidental needle sticks with a used hypodermic needle can transmit disease. Most prior art needle assemblies have a needle shield. Some needle shields define a rigid sleeve that can be telescoped distally over the needle cannula. This procedure requires a healthcare worker to hold the needle assembly or the associated medical implement in one hand and the shield in the other. Some medical procedures require the application of pressure to the penetration site after the needle has been removed. Thus, healthcare workers are often unable to use both hands for shielding the needle cannula. In these situations, workers merely deposit the used medical implement on a nearby surface with the intention of disposing or shielding at a more convenient time. However, until the needle is shielded or properly disposed, the device presents a potential danger to other people.

A needle shield which is hinged near the base of the needle has the advantage of allowing one-handed needle reshielding, thus providing the opportunity for reshielding, under most circumstances, immediately after use.

A hinged needle shield which permanently locks when it is pivoted to the closed needle shielding position has certain advantages. Primarily, there is no doubt about the status of the needle shield assembly and the healthcare worker knows that the needle should be carefully disposed of and not used for further fluid transfer. This is analogous to the prior art rigid cylindrical needle shield which is telescoped over the needle cannula and frictionally engages the needle hub. It is clear with the prior art needle assembly whether the needle is shielded or not shielded. However, having a permanently lockable hinged needle shield presents a problem in situations where the needle is intended to be used twice. For example, the needle is first used to penetrate the pierceable stopper of a medication vial for the purpose of filing the syringe with medication for subsequent injection into a patient. The needle shield assembly with attached syringe is then transported to the patient area for injection of the medication. If the needle is re-shielded permanently after the syringe is filled it cannot be used for injection and a second needle must be installed at the time of use.

It is advantageous to have a self-contained needle shield assembly wherein the adapter for the medical implement, the needle cannula, and the needle shield are all connected in one unit. The prior art includes syringes having cylindrical sleeves over their outside diameter. After injection, the sleeve is advanced to a locked needle protecting position. The syringes are important safety devices, however, not all syringes are used with a needle. The use of a self-contained needle shield assembly allows the end user to attach the needle assembly onto a variety of syringe sizes and to inventory standard syringes for all uses. Accordingly, a more costly safety syringe would not have to be used for applications where the safety features are not necessary.

It is also advantageous to have an enclosed needle cover that protects the cleanliness of the needle even after the needle shield assembly is removed from its sterile package. An enclosed needle cover protects all sides of the needle while a hinged needle shield has one open side and exposes the needle to airborne particles.

Although the prior art provides many improved needle shield devices, there is still a need for a self-contained needle shield assembly wherein the needle shield can be positioned in the needle shielding position using a one-handed procedure and the needle shield automatically locks in the needle shielding position and is unable to be reused. There is a need for a self-contained needle shield assembly which allows the needle to be used twice, once for withdrawing medication into a syringe and then for injecting the medication into a patient wherein the needle may be shielded between the first and second use. There is a need for a needle shield assembly which protects the cleanliness of the needle after the needle shield assembly is removed from its sterile package. There is also a need for a needle shield assembly that provides the shortest possible fluid path between the syringe barrel and the needle tip to avoid loss of medication in the fluid path which cannot be expelled.

SUMMARY OF THE INVENTION

A needle shield assembly having a single-use lock of the present invention includes a needle cannula having a proximal end, a distal end and a lumen therethrough. A hub includes a proximal end for connection to a fluid transfer device and a distal end connected to the proximal end of the needle cannula is connected to a collar. An elongate rigid needle cover is removably engaged to said hub and covers the needle cannula. An elongate needle shield having a proximal end and a distal end is connected, through its proximal end, to the collar. The needle shield includes two side walls defining a longitudinal opening. The needle shield is capable of pivoting from an open position wherein the needle cannula is exposed, to a closed needle protecting position wherein the needle cannula is within the longitudinal opening of the needle shield. The needle shield assembly further includes means for preventing the needle shield from pivoting into the closed position unless the needle cover is removed, and means for automatically and permanently locking the needle shield in the closed needle protecting position when the needle shield is pivoted into the closed position. The means for locking includes a locking arm at the proximal end of the needle shield, a locking pin on one of said collar or said locking arm and a locking aperture on the other of said collar or said locking arm positioned so that when said needle shield is pivoted to the closed needle protecting position the locking arm is deflected outwardly until the locking pin engages the locking aperture.

BRIEF DESCRIPTION OF THE DRAWINGS

FIG. 2 is an exploded view illustrating the assembly of the needle shield assembly of the present invention and a syringe.

FIG. 3 is a perspective view of a needle shield and collar assembly for use in the present invention.

FIG. 4 is a cross-sectional view of the needle shield of FIG. 1 taken along lines 4—4.

FIG. 5 is a cross-sectional view of the needle shield of FIG. 3 taken along lines 5—5.

FIG. 6 is a side elevation view of the needle shield assembly of the present invention attached to a syringe at the time of first use.

FIG. 7 is a side elevation view of the needle shield assembly of the present invention after use with the needle shield in the closed position.

FIG. 8 is a perspective view of an alternative needle shield and collar assembly for use with a needle shield assembly of the present invention.

FIG. 9 is a cross-sectional view of the needle shield of FIG. 8 taken along lines 9—9.

FIG. 10 is a cross-sectional view of the needle shield of FIG. 9 taken along lines 10—10.

DETAILED DESCRIPTION

Figure 1:
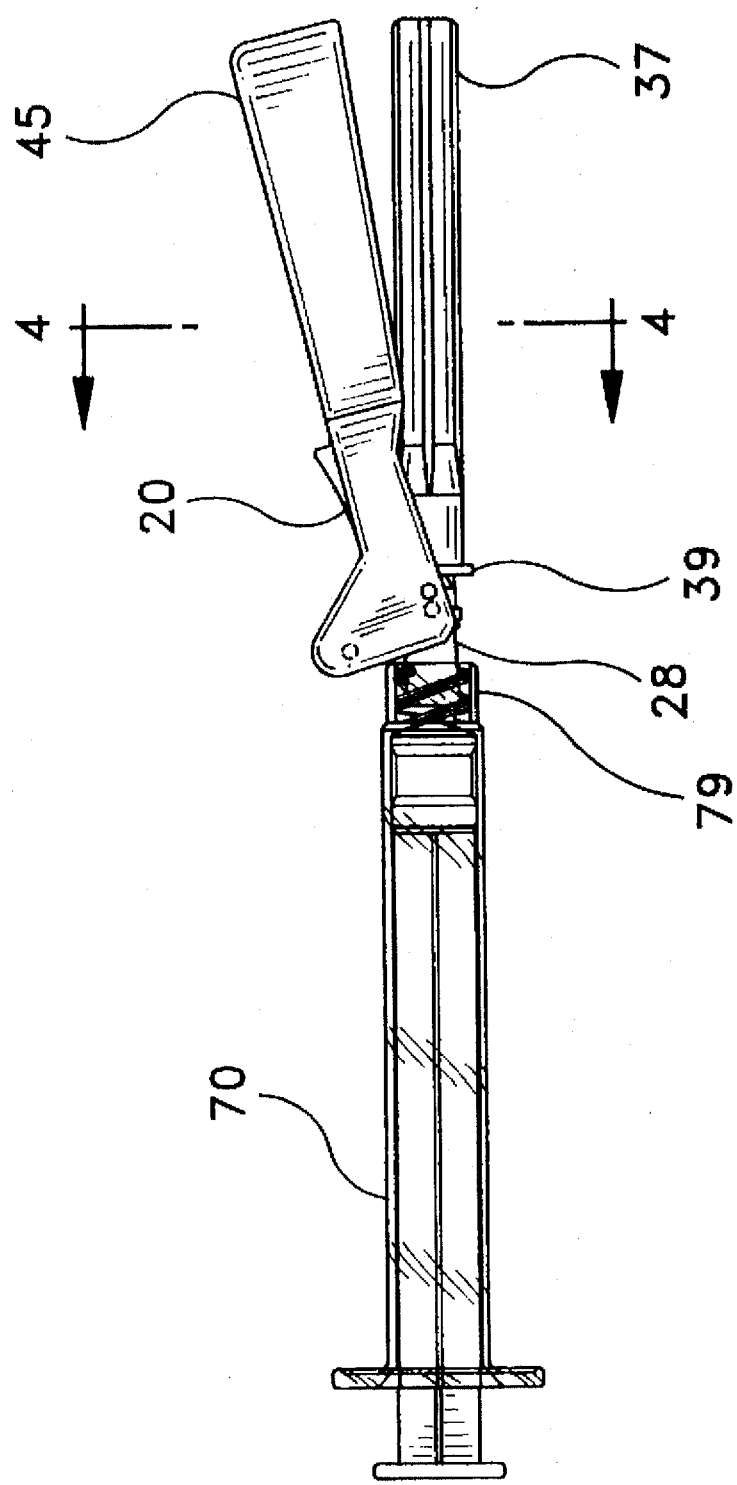
FIG. 1 is a side elevation view of the needle shield assembly of the present invention attached to a syringe before being used.

While this invention is satisfied by embodiments in many different forms, there are shown in the drawings and will be herein described in detail preferred embodiments of the invention with the understanding that the present disclosure is to be considered exemplary of the principles of the invention and not intended to limit the scope of the invention to those embodiments illustrated. The scope of the invention will be measured by the appended claims and their equivalents.

Adverting to FIGS. 1–7, a needle shield assembly having a single-use lock, such as needle shield assembly 20, includes a needle cannula 21 having a proximal end 22, a distal end and a lumen therethrough defining a longitudinal axis 25. In this preferred embodiment, the distal end of the needle cannula includes sharpened tip 26. It is within the purview of the present invention to include blunt cannula which are cannula without sharp tips. Blunt cannula are known in the art and are usually used to inject liquid into an I.V. set or other fluid path having an access port with a pre-slit septum. The blunt cannula is forced through the slit in the septum and into fluid communication with the fluid flow path. Upon removal of the blunt cannula, the slit portion of the septum automatically seals itself.

A hub 28 includes a proximal end 29 and a distal end 31 connected to proximal end 22 of the needle cannula. A collar 41 is connected to the hub. There are many ways of connecting the collar to the hub, such as through interference fit, adhesives, ultrasonic welding and the like. It is within the purview of the present invention to include a hub and collar which are of a unitary one-piece structure. The one-piece structure may be accomplished by many methods including injection molding the collar and base member as a one-piece unit thereby eliminating the need to assemble the base member to the hub during the manufacturing process. In this preferred embodiment, the collar is rotationally connected to the hub in a snap-fit arrangement which allows the collar, through application of manual force, to be rotated around the hub. The rotational connection of the collar and hub is accomplished by interaction between structure on the hub including proximal raised portion 32, distal raised portion 33 and collar receiving recess 34 and the collar. The distance across proximal raised portion 32 and distal raised portion 33 is greater than the inside diameter of collar 41 and greater than the diameter or distance across recess 34. During assembly, the collar is passed over the distal end of the hub and forced over distal raised portion 33 so that it snaps into the spice between raised portion 32 and raised portion 33 and is trapped in that position. It is preferred that there be a certain amount of frictional engagement between the collar and the hub so that the collar cannot rotate freely with respect to the hub. This can be accomplished in many ways, such as, by making the distance between raised portion 32 and raised portion 33 less than the thickness of collar 41 and/or making the diameter or distance across recess 34 slightly larger than the inside diameter of the collar. The advantages of rotationally connecting the collar to the hub will be explained in more detail hereinafter.

An elongate rigid needle cover 37 having a cylindrically-shaped side wall 38 and an open proximal end 39 removably engages hub 28 and covers needle cannula 21, as best illustrated in FIG. 1. A needle cover is an important advantage of the present invention. Preferably, the needle assembly is manufactured and sterilized in a protective package with the needle cover in place. The needle cover provides a contamination barrier for the needle after the needle shield assembly is removed from the sterile package. Accordingly, the user is assured of a clean needle at the time of first use. At the time of first use, the needle cover is removed, as illustrated in FIG. 6, by overcoming engagement forces between the needle hub and the open proximal end of the needle cover.

An elongate needle shield 45 having a distal end 46 and a proximal end 47 is hingedly connected to collar 41. In this preferred embodiment, needle shield 45 is hingedly connected to collar 41 through living hinge 44. It is within the purview of the present invention to include any structure for hingedly connecting the shield to the collar so that the needle shield may be pivoted with respect to the collar. These structures include known mechanical hinges and various linkages, or combinations of hinges and linkages. Needle shield 45 includes two side walls 50 and 51 defining a longitudinal opening 52 and a back wall 53.

The needle shield assembly of the present invention is suitable for use with a wide variety of fluid transfer devices such as syringes, catheters, blood collection devices, tubing sets for blood collection and delivery and the like. For the purpose of illustration, needle shield assembly 20 is illustrated connected to hypodermic syringe 70 comprising a syringe barrel 71 having a distal end 73, a proximal end 74 and a circular side wall 75 defining a chamber 76 for retaining fluid. The distal end of the syringe barrel is connected to the hub so that the lumen of the needle cannula is in fluid communication with chamber 76 of the syringe barrel. In this embodiment, distal end 73 of the syringe barrel includes a frusto-conically shaped tip 77 having a passageway therethrough which provides a fluid path between the cannula and the chamber. The frusto-conically shaped tip of the syringe barrel frictionally engages a frusto-conically shaped cavity in the needle hub. The distal end of the syringe barrel also includes a locking luer-type collar 79 concentrically surrounding the tip. The luer collar has an internal thread which engages the needle hub to hold it securely to the barrel. It is within the scope of the present invention to include various hub configurations to attach to a wide variety of medical or other fluid handling devices. The hub configuration described hereinabove, having a frusto-conically shaped interior cavity, reflects one of these many possibilities. Many syringes, fluid handling devices, such as stopcocks and adapters, and other fluid handling devices contain luer slip and locking luer-type fittings to which the hub of a frusto-conically shaped interior cavity will properly engage. It is also within the purview of the present invention to provide a needle shield assembly wherein the hub is integrally molded with the syringe barrel.

It is an important feature of the present invention that all elements of the needle shield assembly are connected to the hub and that the hub is capable of directly connecting to a fluid handling device such as a syringe. Some prior art devices contain a separate housing which mounts between the needle hub and the syringe, wherein the needle shield is hingedly connected to the separate housing. A separate housing lengthens the fluid flow path between the chamber in the syringe and the distal end of the needle cannula thereby wasting medication, because it cannot be expelled, the fluid flow path through the housing must be filled with medication before medication can leave the proximal end of the needle. In some cases, the medication may cost one hundred times more than the syringe and small amounts of medication lost over a substantial number of syringes can result in a substantial unnecessary loss of valuable medication. Also, the additional element increases the length between the syringe and the needle tip possibly making it slightly more difficult to accurately position the needle, for example in a patient's vein.

Needle shield 45 is capable of pivoting from an open position wherein needle cannula 21 is exposed, as best illustrated in FIG. 6, to a closed needle protecting position wherein the needle cannula is within the longitudinal opening of the needle shield, as best illustrated in FIG. 7.

As will be explained in more detail hereinafter, an important feature of the present invention includes means for preventing the needle shield from being pivoted into the closed position before the needle cover is removed. In this preferred embodiment means for preventing is accomplished forming at least a portion of the side walls so that the longitudinal opening is smaller than the needle cover, so that the needle cover must be removed before the needle shield can be pivoted into the closed needle protecting position. It is within the scope of the present invention to include many structures which prevent the movement of the needle shield into the closed needle protecting position before the needle cover is removed. Such structures may include a projection on the needle shield, the needle cover or on both elements which creates an interference between the needle shield and the needle cover which prevents moving the needle shield into the closed needle protecting position.

Another important feature of the present invention includes means for automatically locking the needle shield in the closed needle protecting position when the needle shield is pivoted into the closed position. "Automatically" is intended to mean that movement of the needle shield sufficiently into the needle protecting position will cause locking to occur automatically without further action on behalf of the user. "Permanently" is intended to mean that there is no unlocking structure, and the needle will remain shielded until proper disposal. The lock should generally withstand the normal forces encountered during proper disposal of the needle shield assembly.

In this preferred embodiment, means for automatically and permanently locking the needle shield in the closed needle protecting position includes two parallel opposed locking arms 55 and 56 at the proximal end of the needle shield containing locking apertures 57 and 58 respectively. The collar further includes two opposed locking pins 61 and 62. The locking arms are shaped and positioned so that when the needle shield is pivoted to the closed needle protecting position, the locking arms are deflected outwardly until locking pins 61 and 62 engage locking apertures 57 and 58 respectively, to permanently lock the needle shield in the closed position. It is within the purview of the present invention to have less than and more than two locking arms and the related structure for locking the needle shield in a closed position. For example, the present invention may include at least one locking arm at the proximal end of the needle shield, a locking pin positioned on one of the locking arm or the collar and a locking aperture in the other of the collar or the locking arm, so that when the needle shield is pivoted into the closed needle protecting position the locking arm is outwardly until the locking pin engages the locking aperture.

As best illustrated in FIG. 7, it is preferred that when the needle shield is in the closed position, the needle shield should be pivoted far enough so that back wall 53 contacts and possibly slightly deflects needle cannula 21. This contacting relationship assures that the needle cannula is positioned in the needle shield as deeply as possible to minimize the chance of re-exposing the needle through minor deflection of the needle shield.

Referring to FIGS. 6 and 7 it can be seen that the needle shield can be moved from the open position to the closed position using a single-handed procedure. For example, by grasping syringe 70 with the fingers and advancing the needle shield from the open position to the closed position by pressing on the back wall with the thumb until the needle shield is in the closed locked position. To facilitate the single-handed operation of the needle shield, finger pad 69 is provided at the proximal end of the needle shield.

It is desirable to have means for releasably retaining the needle shield in the opening position. Holding the needle shield in the open position keeps it from interfering with the injection process either visually or physically. Releasably retaining the needle shield in the open position may be accomplished by dimensioning parts of the assembly so that friction is created in the hinge or by using an articulated over-center hinge or by creating some interference between the needle shield and the collar which must be forcefully overcome to move the needle shield out of the open position. In this embodiment, existing structure is used to accomplish this result. In particular, locking pins 61 and 62 engage concave detents 63 and 64 respectively when the needle shield is in the open position. Additional force is required to pivot the needle shield out of the open position. In the open position it is preferred that longitudinal opening 52 be oriented from between about 90° to 180° from longitudinal axis 25 of the needle cannula, as best illustrated in FIG. 6, where the needle shield is rotated so that longitudinal opening 52 is about 150° from longitudinal axis 25 of the needle cannula.

As best illustrated in FIG. 6., sharpened tip 26 of needle cannula 21 is sharpened to a bevel shape having a bevel surface 27 oriented at angle A with respect to longitudinal axis 25. Bevel surface 27 faces direction B. The rotational connection of the collar to the hub is an important feature of the present invention because it allows rotation of the needle shield so that the bevel surface faces the same side of the collar as the needle shield when the needle shield is in the open position. Rotation of the needle shield to this position makes it easier to insert the needle into a patient's vein. Accordingly, it is desirable to have bevel surface 27 facing the same side of the needle assembly as the needle shield when the needle shield is in the open position, so that the needle shield does not interfere with positioning the syringe close to the patient's body, for example, the patient's arm, when attempting to gain access into a vein. The needle shield can also be positioned on the same side of the needle shield as the bevel by designing the elements and/or the manufacturing process so that the assembly of the needle shield assembly achieves this result.

FIG. 1 illustrates needle shield assembly 20 connected to hypodermic syringe 70 in a configuration in which it is likely to be delivered, in sterile form, from a manufacturer. Placing needle shield 45 in an intermediate position between the closed position and the open position, closer to the closed position, creates a configuration which takes up less packaging and shipping carton space. This is especially true when the needle shield assembly is being shipped separately without being attached to a fluid delivery instrument such as a syringe. Also, in this intermediate position, the needle shield assembly is easier to handle for the purposes of installing it onto a fluid delivery device, such as screwing the hub onto a standard locking luer-type fitting. Accordingly, it is desirable to provide means for releasably retaining the needle shield in an intermediate position between the open position and the closed position. In this preferred embodiment means for releasably retaining the needle shield in the intermediate position includes concave detents 67 and 68 in locking arms 55 and 56 respectively. Concave detents 67 an 68 function exactly as concave detents 63 and 64 which cooperate with locking pins 61 and 62 to hold the needle shield in the open position. However, detents 67 and 68 hold the needle shield in intermediate position and require additional force to pivotably move the needle shield from the intermediate position.

FIGS. 8–10 illustrate an alternative needle shield and collar assembly for use with the needle shield assembly of the present invention. The alternate needle shield and collar function similarly to the needle shield and collar assembly of FIGS. 1–7 except that the position of locking apertures, locking pins and detents have been reversed.

Alternate needle shield and collar assembly 80 includes a collar 141 and a needle shield 145 hingedly connected to the collar through a hinge 144. Means for locking the needle shield in the closed needle protecting position includes two parallel opposed locking arms 155 and 156 at the proximal end of the needle shield, and locking pins 161 and 162 in each arm respectively. Collar 41 includes two opposed locking apertures 157 and a second aperture, not illustrated, on the opposite side of the collar as aperture 157. The locking arms are positioned so that when the needle shield is pivoted to the closed needle protecting position, the locking arms are deflected outwardly until the locking pins engage the locking apertures to permanently lock the needle shield in the closed position. Means for releasably retaining the needle shield in the open position includes convex or raised detents 163 and 164 which engage locking apertures 157 and 158 respectively when the needle shield is in the open position. The word detent as used herein is intended to include concave detents and convex detents whichever are appropriate to cooperate with the opposing structure to provide the releasably retaining function. Likewise, convex detents such as convex detent 168 are provided to hold the needle shield in the intermediate position in a similar fashion as described for the embodiment of FIGS. 1–7.

It can be seen that the present invention provides a self-contained needle shield assembly wherein the needle shield can be positioned in the needle shielding position using a one-handed procedure and the needle shield automatically locks in the needle shielding position so that the needle is unable to be reused. The needle shield assembly of the present invention also provides structure to protect the sterility and cleanliness of the needle until the needle is first used. The present invention also provides a self-contained needle shield assembly which allows the needle to be used twice, once for withdrawing medication into a syringe and then for injecting medication into a patient while providing means for preventing the permanent locking of the needle shield until the final use by preventing the needle shield from being pivoted into the closed position while the needle cover is installed.

What is claimed is:

1. A needle shield assembly having a single-use lock comprising:
    a needle cannula having a proximal end, a distal end and a lumen therethrough;
    a hub having a proximal end for connecting to a fluid transfer device and a distal end connected to said proximal end of said needle cannula;
    a collar connected to said hub;
    an elongate rigid needle cover removably engaging said hub and covering said needle cannula;
    an elongate needle shield having a distal end and a proximal end hingedly connected to said collar
    said needle shield including two side walls defining a longitudinal opening, said needle shield capable of pivoting from an open position wherein said needle cannula is exposed, to a closed needle protecting position wherein said needle cannula is within said longitudinal opening of said needle shield;
    means for preventing said needle shield from being pivoted into said closed position while said needle cover is engaging said hub;
    means for automatically and permanently locking said needle shield in said closed needle protecting position when said needle shield is pivoted into said closed position, said means for locking including a locking arm at said proximal end of said needle shield, a locking pin on one of said collar or said locking arm and a locking aperture the other of said collar or said locking arm positioned so that when said needle shield is pivoted to said closed needle protecting position said locking arm is deflected outwardly until said locking pin engages said locking aperture.

2. The needle shield assembly of claim 1 wherein said means for preventing includes at least a portion of said side walls being formed so that said longitudinal opening is smaller than said needle cover so that said needle cover must be removed before said needle shield can be pivoted to said closed position.

3. The needle shield assembly of claim 1 wherein said means for locking includes a second locking arm opposed from said locking arm and a second locking pin on one of said second locking arm or second collar, and a second locking aperture on the other of said second locking arm or said collar.

4. The needle shield assembly of claim 1 further including means for releasably retaining said needle shield in said open position.

5. The needle shield assembly of claim 4 wherein said means for releasably retaining said needle shield in said open position includes a detent in said locking arm which engages said locking pin when said needle shield is pivoted to said open position.

6. The needle shield assembly of claim 4 wherein the longitudinal opening of the needle shield is positioned between about 90° to 180° from said longitudinal axis of said needle cannula when said needle shield is in said open position.

7. The needle shield assembly of claim 1 further including means for releasably retaining said needle shield in an intermediate position between said open position and said closed position.

8. The needle shield assembly of claim 7 wherein said means for releasably retaining said needle shield in said intermediate position includes a detent in said locking arm which engages said locking pin when said needle shield is in said intermediate position.

9. The needle shield assembly of claim 1 wherein said distal end of said needle cannula includes a sharp tip.

10. The needle shield assembly of claim 9 wherein said sharp tip is bevel-shaped having a bevel surface.

11. The needle shield assembly of claim 10 wherein said bevel surface faces the same side of said collar as said needle shield when said needle shield is in said open position.

12. The needle shield assembly of claim 1 wherein said collar is rotationally connected to said hub so that said collar can be rotated around said hub.

13. The needle shield assembly of claim 1 wherein said collar and said needle shield are connected by a living hinge and made of a unitary one-piece construction.

14. The needle shield assembly of claim 1 further including a syringe barrel having a distal end, a proximal end and a circular side wall therebetween defining a chamber for retaining fluid, said distal end of said syringe barrel being connected to said hub so that said lumen in said needle cannula is in fluid communication with said chamber.

15. The needle shield assembly of claim 14 wherein said hub and said syringe barrel are made of a unitary one-piece construction.

16. The needle shield assembly of claim 1 wherein said needle shield includes a back wall between said two side walls and opposite said longitudinal opening.

17. The needle shield assembly of claim 15 wherein said back wall contacts said needle cannula when said needle shield is in said closed position.

18. A needle shield assembly having a single-use lock comprising: a needle cannula having a proximal end, a distal end and a lumen therethrough defining a longitudinal axis, said distal end of said needle cannula including a sharp tip;
   a hub having a proximal end for connecting to a fluid transfer device and a distal end connected to said proximal end of said needle cannula;
   a collar rotationally connected to said hub so that said collar can be rotated around said hub;
   an elongate rigid needle cover releasably engaging said hub and covering said needle cannula;
   an elongate needle shield having a distal end and a proximal end hingedly connected to said collar, said needle shield including two side walls defining a longitudinal opening and a back wall between said sidewalls opposite said longitudinal opening, said needle shield capable of pivoting from an open position wherein said needle cannula is exposed, to a closed needle protecting position wherein said needle cannula is within said longitudinal opening of said needle shield;
   at least a portion of said longitudinal opening being smaller than said needle cover so that said needle cover must be removed before said needle shield can be pivoted to said closed position;
   said needle shield including two parallel opposed locking arms at its proximal end and a locking aperture in each locking arm, said collar including two opposed locking pins, said locking arms being positioned so that when said needle shield is pivoted to said closed needle protecting position, said locking arms are deflected outwardly until said locking pins engage said locking apertures to permanently lock said needle shield in said closed position.

19. The needle shield assembly of claim 18 wherein the positions of the locking pins and locking aperture are reversed and said collar includes two opposed locking apertures and said locking arms each include an inwardly directed locking pin.

20. The needle shield assembly of claim 18 wherein said back wall contacts said needle cannula when said needle shield is in said closed position.

* * * * *